(12) United States Patent
Baldwin et al.

(10) Patent No.: US 6,243,164 B1
(45) Date of Patent: Jun. 5, 2001

(54) METHOD AND SYSTEM FOR DETERMINING LEAD COPLANARITY

(75) Inventors: Leo B. Baldwin, Beaverton; Michael P. Kelley, Lake Oswego, both of OR (US)

(73) Assignee: Electro Scientific Industries, Portland, OR (US)

( * ) Notice: Subject to any disclaimer, the term of this patent is extended or adjusted under 35 U.S.C. 154(b) by 0 days.

(21) Appl. No.: 09/348,238

(22) Filed: Jul. 6, 1999

Related U.S. Application Data

(60) Provisional application No. 60/092,628, filed on Jul. 13, 1998.

(51) Int. Cl.[7] .................................................. G01N 21/88
(52) U.S. Cl. ........................................ 356/375; 356/237.1
(58) Field of Search .................................. 356/375, 394, 356/237.1, 237.2; 29/833, 705; 228/180.21; 250/559.29, 559.34; 348/125, 126, 129

(56) References Cited

U.S. PATENT DOCUMENTS

| | | | |
|---|---|---|---|
| 4,736,108 | * 4/1988 | Comstock et al. | 250/561 |
| 4,827,436 | * 5/1989 | Sabersky et al. | 356/372 |
| 4,959,898 | * 10/1990 | Landman et al. | 29/705 |
| 5,249,239 | * 9/1993 | Kida | 382/8 |
| 5,305,894 | 4/1994 | McGarvey | 209/580 |
| 5,331,406 | * 7/1994 | Fishbaine et al. | 356/375 |
| 5,440,391 | 8/1995 | Smeyers et al. | 356/375 |
| 5,452,080 | * 9/1995 | Tomiya | 356/237 |
| 5,481,203 | * 1/1996 | Appold | 324/755 |
| 5,563,703 | 10/1996 | Lebeau et al. | 356/237 |
| 5,636,025 | 6/1997 | Bieman et al. | 356/374 |
| 5,897,048 | 4/1999 | Cheng et al. | 228/180.5 |
| 6,055,055 | * 4/2000 | Toh | 356/376 |

* cited by examiner

Primary Examiner—Hoa Q. Pham
(74) Attorney, Agent, or Firm—Stoel Rives LLP

(57) ABSTRACT

The coplanarity of leads (14) of an integrated circuit (IC) in a surface-mount technology package (SMT) (10) can be determined by means of a plurality of views without the use of a conventional pedestal (20), without the use of an associated Z-axis actuator, and without the associated delays required to deploy such a Z-axis actuator. In the invention, three leads (14) of SMT package (10) are arbitrarily selected to define a virtual reference plane (50) in a first or virtual coordinate system, and the positions of the unselected leads are measured with reference to the virtual reference plane (50). For convenience, the virtual reference plane (50) can be defined as Z=0 and may have height coordinates in Z that are negative or positive with respect to the virtual reference plane (50). The virtual coordinates are analyzed, and three leads (14) having the lowest Z coordinates are determined to define a virtual sitting plane (60). For convenience, the virtual sitting plane (60) can be defined as Z=0 in a second or real coordinate system. A mathematical transformation that relates the first coordinate system to the second coordinate system is determined, and the coordinates for each lead (14) of SMT package (10) are subsequently transformed from the first coordinate system to the second coordinate system. In the second coordinate system, each Z coordinate directly corresponds to the lead standoff value (64) that largely determines the acceptability of the inspected SMT package (10). A variety of techniques are optionally employed to determine whether SMT package (10) is bi-stable.

37 Claims, 5 Drawing Sheets

METHOD AND SYSTEM FOR DETERMINING LEAD COPLANARITY

This application derives priority from U.S. Provisional Application No. 60/092,628, filed Jul. 13, 1998.

TECHNICAL FIELD

This invention relates to machine vision systems for inspecting integrated circuits and, in particular, to a method and apparatus for inspecting the leads of packaged integrated circuits.

BACKGROUND OF THE INVENTION

Machine vision is the analysis of images by a computing device such that some determination can be made about a scene or object that is viewed by an image sensor or sensors connected directly or indirectly to the computing device.

Electronic integrated circuits (ICs) are generally enclosed in plastic or ceramic packages of a generally rectangular parallelepipedal hexahedral shape. These packages include a plurality of leads about the periphery to provide electrical contact to the circuits within the package, and the leads include a means for attachment to a printed wire circuit board that typically forms part of a larger assembly of similar integrated circuits and other electronic components.

The old standard practice generally deployed the leads to protrude from the top and/or bottom major surfaces of the package such that all the leads were oriented in a direction normal to the plane of the major surfaces of the package. These leads were then inserted through corresponding holes in the printed wire board for mechanical and electrical attachment by soldering. These packages are known in the art as through-hole packages.

In the last 10 to 15 years, conventional practice has transitioned to deploying the leads about the periphery of the IC package in a plane parallel to the package with the distal portions of the leads offset from the plane of the package. The distal portions of the leads are then positioned on corresponding pads on the printed wire boards for soldering. This technique allows closer spacing of the leads, a reduction in size of the overall package, and the placement of IC packages on both sides of the printed wire board. These packages are known in the art as surface-mount-technology (SMT) packages.

FIG. 1 is an isometric view showing a conventional SMT package 10 having a defective lead 12 among a plurality of leads 14a–14j (collectively or generically, 14) that protrude from major side surfaces 16 and/or minor side surfaces 17 of a plastic or ceramic casing 18. With reference to FIG. 1, for each lead 14 of SMT package 10 to be successfully soldered to a substantially planar printed wire board (not shown), leads 14 should all be substantially within the same plane, a property known in the art as lead coplanarity. For example, a defective or noncoplanar lead 12 may exhibit a property known in the art as lead standoff, a defect characterized by a lead 12 that sits too high above a printed wire board for a reliable solder connection to be made between the lead 12 and a corresponding copper pad on the printed wire board.

The methods of determining the coplanarity of leads 14 of SMT packages 10 can be divided for the purposes of discussion into two groups: those that can generate a three-dimensional surface map of an object with one view and those that synthesize a three-dimensional map of the object viewed by combining the information from a plurality of two-dimensional maps.

The first group includes techniques that use a particular type of illumination with a property that renders a two-dimensional image with additional information on the distance of each point in the image from the image sensor. Examples of such techniques include structured lighting techniques, scan-angle modulated techniques, moire techniques, interferometric techniques, holographic techniques, and time-of-flight techniques. For example, Beiman and Michniewicz disclose a moiré interferometry technique for measuring surface contours of an object in U.S. Pat. No. 5,636,025.

The second group uses a plurality of two-dimensional images that are generated by a plurality of two-dimensional image sensors such as conventional video cameras and uses the a priori knowledge of the positions of the image sensors to mathematically construct the three-dimensional nature of the object viewed.

As a convenience, to reduce the size of the coplanarity sensing device, and as an economic measure to reduce the number of image sensors required, two or more of the required views may be combined by mirrors or by prisms, or by a combination of both, onto a single two-dimensional image sensor.

For example, Lebeau and Hopkins disclose a technique employing at least one mirror and a pedestal 20 that serves as a physical reference plane 22 for determining SMT lead coplanarity in U.S. Pat. No. 5,563,703 ('703 patent). Smeyers and Vanderheydt similarly disclose a technique employing a plurality of mirrors, a pedestal 20 that serves as a physical reference plane 22, and a diffusive top surface 24 upon which a shadow of leads 14 are cast from a plurality of angles to determine SMT lead coplanarity in U.S. Pat. No. 5,440,391 ('391 patent). In FIG. 1 and with reference to the '703 and '391 patents, the top surface 24 of pedestal 20 provides the reference plane 22, which is also commonly known as the Z-axis reference plane 22. The height, or Z coordinate, for each lead 14 is then determined with respect to the physical reference plane 22.

These inspection systems require specialized handling devices, such as a Z-axis actuator, capable of deploying an SMT package 10 along a specified axis or path to position SMT package 10 to be substantially in contact with and coplanar with the surface 24 of pedestal 20 at a predetermined fixed location that is within a view of an image sensor. The view is from above, but not normal to, the physical reference plane 22.

The typical requirement for motion along the physical reference plane places two burdens on SMT package inspection. One burden is the requirement for a Z-axis actuator and its attendant power and control devices. The other burden is the time required to deploy the SMT package 10 in the Z axis onto pedestal 20, the pause required during which the images of SMT package 10 on pedestal 20 are acquired, and the time to reverse the deployment of SMT package 10 from pedestal 20 so that SMT package 10 may resume travel along its original path.

SUMMARY OF THE INVENTION

An object of the present invention is, therefore, to provide a method or system for determining the relative coplanarity of leads of an SMT package.

Another object of the invention is to employ machine vision technology to determine the magnitude of deviations from the coplanarity of leads of the SMT package.

An advantage of the invention is that a plurality of views of the SMT package can determine the relative coplanarity of its leads without the use of a pedestal and without the delays associated with deploying the pedestal.

In a preferred embodiment, a camera provides a first view of an SMT package 10 from an axis substantially normal to the plane of SMT package 10. One or more additional cameras provide one or more additional views of the SMT package 10 from an axis that is substantially collinear with the plane of SMT package 10, such as collinear views for each side of SMT package 10 that exhibits leads 14. The views are combined, and three leads 14 of SMT package 10 are arbitrarily chosen to define a virtual plane in a first coordinate system. The remaining leads 14 are then measured with reference to the virtual plane. For convenience, the virtual plane can be defined as Z=0 and may have height coordinates in Z that are negative or positive with respect to the virtual plane. The virtual coordinates are analyzed, and three leads 14 having the lowest Z coordinates are determined to define a reference plane. In an alternative preferred embodiment, the three lowest leads that circumscribe the center of mass of the package (as projected along the Z axis) are selected as the reference plane. For convenience, the reference plane can be defined as Z=0 in a second coordinate system, which may be referred to as the real coordinate system. A mathematical transformation that relates the first coordinate system to the second coordinate system is determined, and the coordinates for each lead 14 of the SMT package 10 are subsequently transformed from the first coordinate system to the second coordinate system. In the second coordinate system, each Z coordinate directly corresponds to the lead standoff value that largely determines the acceptability of the inspected SMT package 10.

This information can be employed by manufacturers of electronic assemblies including surface-mount IC components and printed wire boards to better control the manufacturing process and also reject SMT packages 10 or components whose leads 14 are noncoplanar beyond acceptable limits where the inclusion of such components in the electronic assemblies would result in nonfunctioning assemblies.

Additional objects and advantages of this invention will be apparent from the following detailed description of preferred embodiments thereof, which proceeds with reference to the accompanying drawings.

DETAILED DESCRIPTION OF PREFERRED EMBODIMENTS

Figure 2:
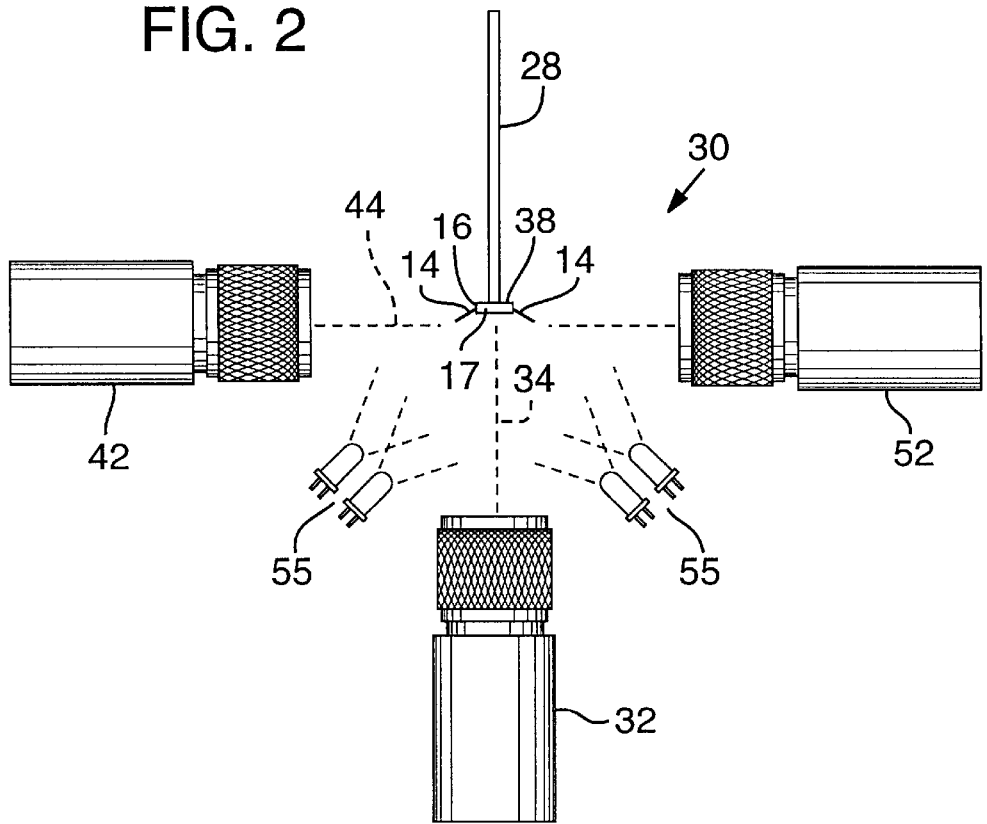
FIGS. 2 and 2A are side elevation view showing an exemplary three-camera system positioned about an SMT package to obtain lead position data.
Figure 3:
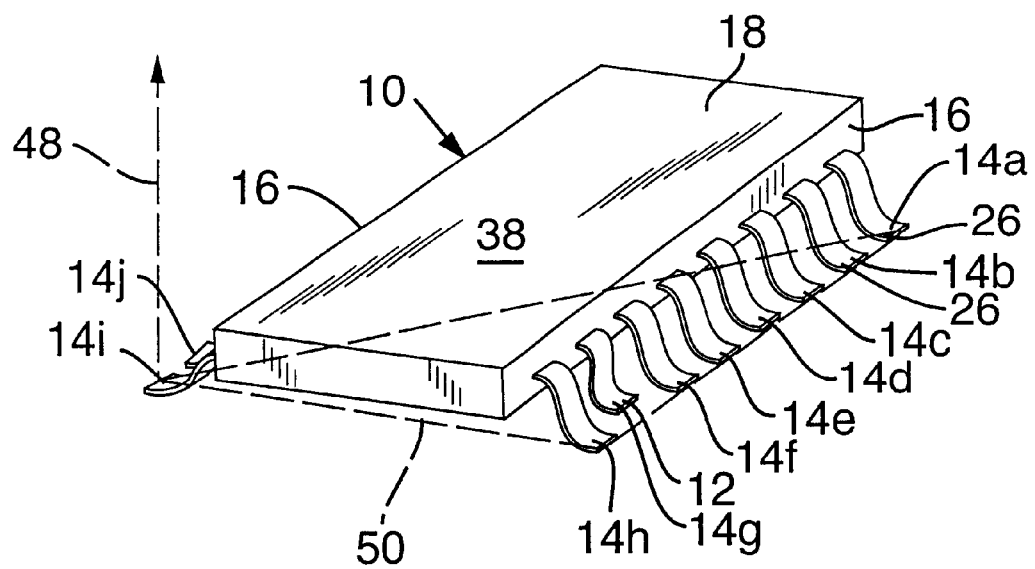
FIG. 3 is an enlarged isometric view of the SMT package of FIG. 1 with a line normal to an exemplary first reference plane defined by a set of three distantly separated leads.

FIG. 2 is a side elevation view showing a package carrier 28 that holds or carries an SMT package 10 through a machine vision system 30, and FIG. 3 is an enlarged view of an SMT package 10. With reference to FIGS. 2 and 3, package carrier 28 preferably employs a vacuum pipette to delicately carry SMT package 10 from one of its top or bottom major surfaces 38 or one of its non-lead side surfaces 17. Alternatively, package carrier 28 can employ clamps, grippers, or other known means to delicately grasp SMT package 10 from both its major surfaces or both its non lead side surfaces 17. Skilled persons will appreciate that SMT package 10 need not have a rectangular parallelepipedal hexahedral shape. SMT package 10 may, for example, have a disklike or other shape.

With reference to FIGS. 2 and 3, machine vision system 30 may be positioned in a predetermined location to obtain position data of distal portions 26 of leads 14, such as J or gull wing leads, that protrude from major side surfaces 16 of SMT package 10. Skilled persons will appreciate that SMT package 10 can alternatively be held steady while machine vision system 30 moves into a predetermined location or both SMT package 10 and machine vision system 30 can be in motion during lead data acquisition.

In a preferred embodiment, machine vision system 30 employs an image sensor 32, such as a two-dimensional image sensor like a video camera or focal plane array sensor, to obtain a view of SMT package 10 from an axis 34 that is preferably substantially normal to an X-Y plane 36 (FIG. 1), which is coplanar or parallel with a major surface 38 of package casing 18. A second image sensor 42 obtains a view of SMT package 10 along a focal plane or axis 44 that is substantially collinear or coparallel with X-Y plane 36 of SMT package 10. The normal and collinear views are then combined to create a virtual three-dimensional representation of SMT package 10, particularly the positions of leads 14, to determine coplanarity of each lead 14 of SMT package 10.

The collinear or coparallel view may include separate or combined views for each major side surface 16 of SMT package 10 that exhibits leads 14. Skilled persons will appreciate that a variety of off-axis views and sensor positions could be substituted for the views selected for the preferred embodiments.

Figure 2A:
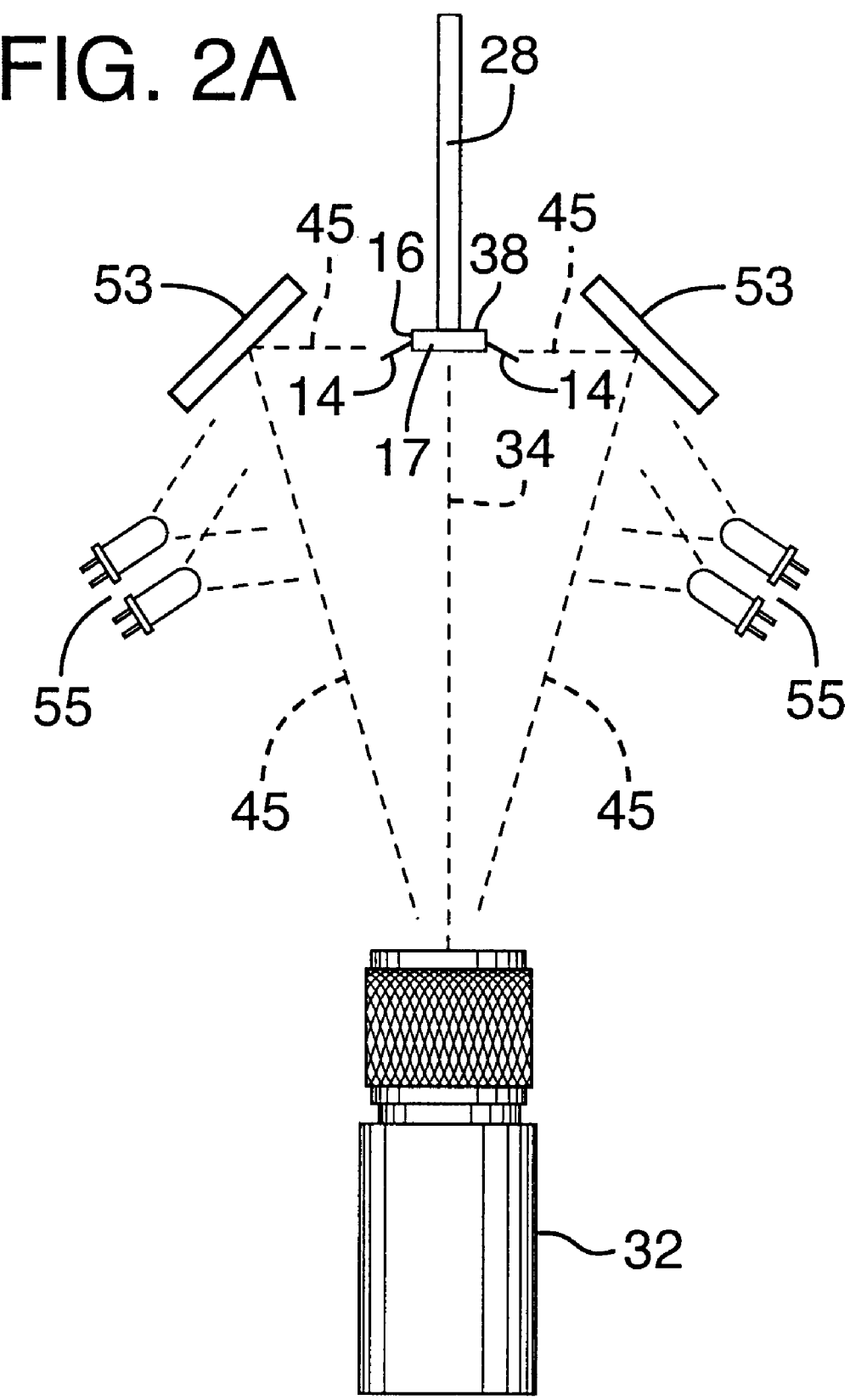

With reference to FIGS. 2 and 2A, skilled persons will also appreciate that the plurality of views may be formed by an equal number of image sensors 32, 42, and 52, or two or more views 45 may be combined onto a single image sensor 32 or 42 by the use of mirrors, prisms, or other optics 53, or their combinations, all of which are familiar to persons skilled in optics. The optical combinations can be manipulated by skilled persons to reduce the size of the overall vision system 30, to reduce the cost of assembly, to integrate with particular lighting techniques, or to facilitate any combination of these goals. Lighting techniques or sources 55 that can be employed to illuminate leads 14 are well known to skilled persons and include, but are not limited to, LEDs, gas tube lamps, fluorescent lamps, electroluminescent sources, or incandescent lamps, each with associated optics and light pipes as appropriate. Short duration light sources or mechanically or electrically shuttered image sensors 32, 42, or 52 can be employed to acquire images of leads 14 in a time span that is sufficiently short to avoid any image degradation due to motion of SMT package 10. Such a short time span would depend on a number of factors such as the speed with which package carrier 28 carries SMT package 10 through the predetermined location or the field of view and the degree to which motion-induced blur should be minimized in order to not degrade system resolution or accuracy. A short duration of time for lighting or image acquisition may be, for example, less than one second. A short-duration image acquisition system is particularly useful for on-the-fly inspection when SMT package 10 is in continuous motion.

In addition, skilled persons will recognize that the elimination of pedestal 20 will permit SMT package 10 to be inspected while in any of a variety of orientations with respect to the ground. For example, SMT package 10 may be inspected upside down, i.e., with its major surface 38 oriented toward the ground. Alternatively, major surface 38 could be oriented vertically. The image sensors 32, 42, and 52 would, of course, be positioned to accommodate the alternative orientation of SMT package 10.

Figure 1:
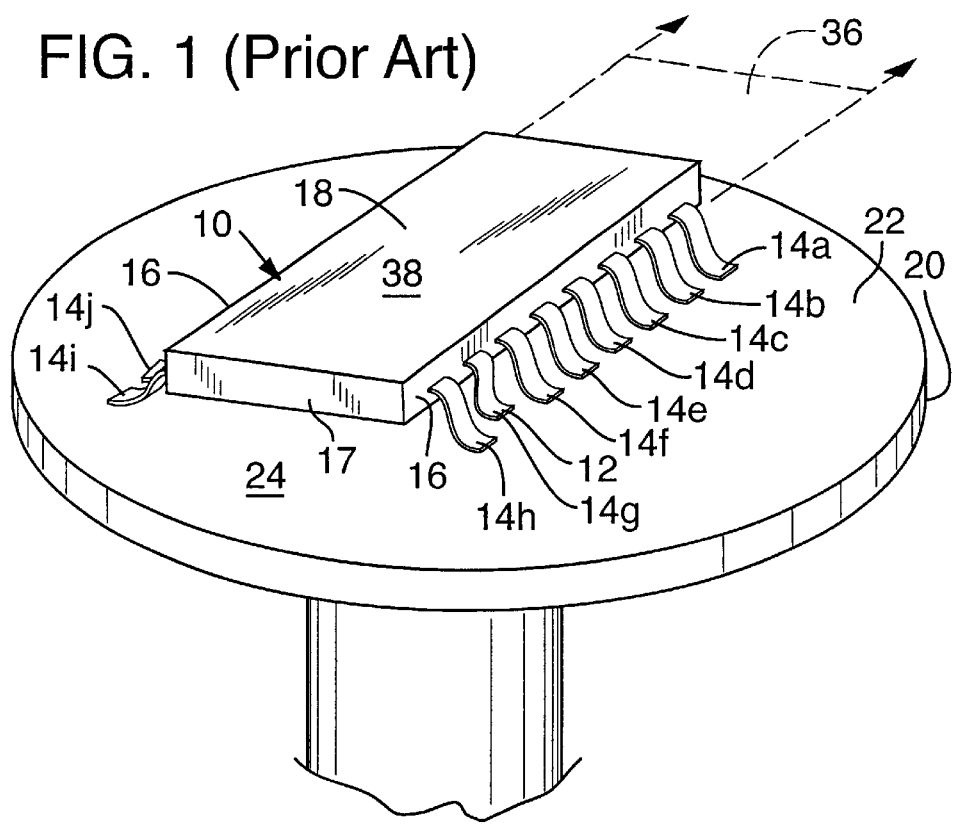
FIG. 1 is an isometric view showing a prior art SMT package having a defective, noncoplanar lead.

FIG. 3 is an enlarged isometric view of the SMT package 10 of FIG. 1 and shows a line 48 that is normal to an exemplary virtual or first reference plane 50 defined by a set of three distantly separated leads 14. With reference to FIGS. 2 and 3, because three points define a plane, a reference set of three leads 14 are arbitrarily chosen to define virtual reference plane 50. For convenience, the reference set is selected to contain three of the most separated leads 14, such as first, second, and third leads 14a, 14h, and 14i, respectively. This selection will help to minimize the effects of the real resolution limits of machine vision system 30. Virtual reference plane 50 may have no specific or special properties. For convenience, virtual reference plane 50 can be labeled as the Z=0 plane in a first or virtual reference coordinate system. With information from the collinear views of SMT package 10, the virtual heights of the distal portions of the remaining leads 14 are then measured with respect to virtual reference plane 50 and may be designated with virtual Z coordinates. The virtual Z coordinates of these remaining leads 14 may be positive or negative with respect to virtual reference plane 50 because it is arbitrary.

Because this invention dispenses with physical reference plane 22 (FIG. 1) and can utilize a variety of information from an SMT package 10 in free space to select an arbitrary or virtual reference plane, skilled persons will appreciate that this arbitrary reference plane is not limited to virtual reference plane 50 and may be above, below, transverse to, or coplanar with casing 18 of the SMT package 10. Skilled persons therefore will also appreciate that the arbitrary or virtual reference plane may incorporate or be determined from either of major surfaces 38, such as plane 36, or utilize information from major or minor side surfaces 16 or 17. Additionally or alternatively, information concerning the focal plane 44 or the focal axes of any of the image sensors may be used to determine the arbitrary or virtual reference plane.

Substantially simultaneously with the determination of virtual reference plane 50, the relative position of each lead 14 with respect to the X-Y plane 36 of the device is determined from the substantially normal view of SMT package 10, such as the view from image sensor 32. These relative positions can be conveniently designated with X and Y coordinates. Thus, for convenience, the relative positions of the distal portions of leads 14 may be designated with Cartesian coordinates in the virtual reference plane 50 in terms of x, y, z. Skilled persons will appreciate that information from the normal view can be used to select the arbitrary or most separated leads 14 used to define the virtual reference plane 50 in real time, or the leads 14 can be arbitrarily preselected.

Figure 4:
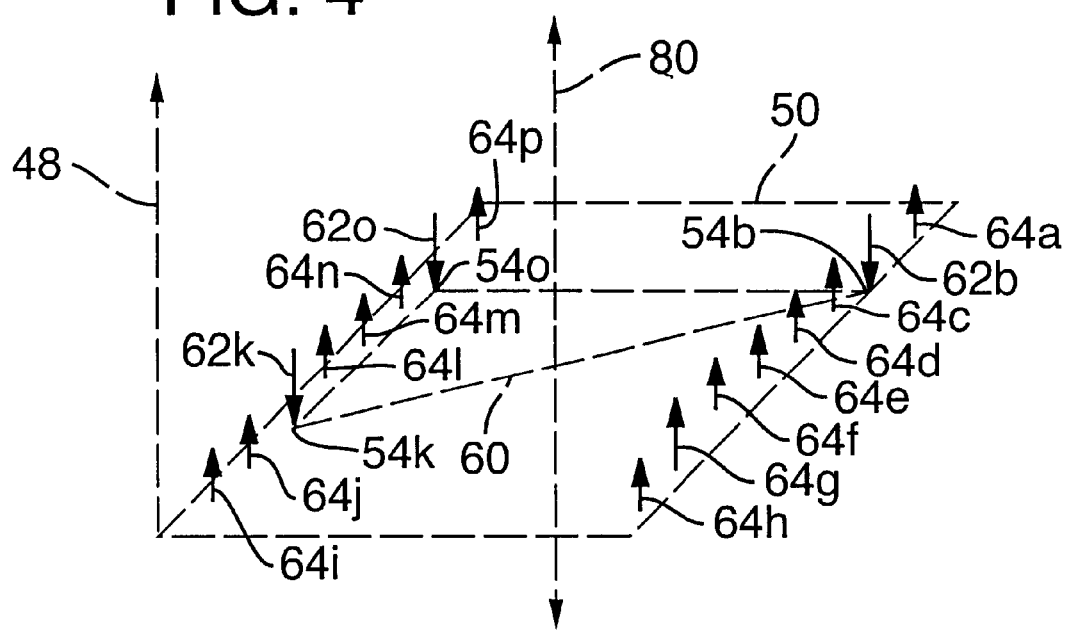
FIG. 4 is a simplified representation of an exemplary second reference plane that is defined with respect to the first reference plane of FIG. 3.

FIG. 4 is a simplified representation of an exemplary second reference plane or virtual sitting plane 60 that is defined with respect to the virtual reference plane 50 of FIG. 3. With reference to FIGS. 3 and 4, the virtual Z coordinates are analyzed to determine a sitting plane set of three leads 14, such as fourth, fifth, and sixth leads 14b, 14k, and 14o, respectively, whose distal portions 26 have the greatest distances 62b, 62k, and 62o and, therefore, the lowest coordinates 54b, 54k, and 54o (collectively or generically, 54), respectively, from casing 18 along respective Z axes. Skilled persons will appreciate that because the virtual reference plane 50 is chosen arbitrarily, it can, but does not necessarily, include one or more leads 14 that are also in the virtual sitting plane 60.

The sitting plane set of leads 14b, 14k, and 14o having the respective lowest coordinates 54b, 54k, and 54o are then used to define the virtual sitting plane 60. Virtual sitting plane 60 can be analogous to the prior art Z-axis physical reference plane 22, which is defined by surface 24 of pedestal 20 that supports SMT package 10 in a conventional lead inspection system. The virtual sitting plane 60 can be conveniently labeled as the Z=0 plane in a second coordinate system (sitting or real coordinate system), and the relative positions of leads 14 may be designated with Cartesian coordinates in the virtual sitting plane 60 in terms of x', y', z'. These second coordinates are offset and generally rotated from the virtual reference plane 50. For example, when SMT package 10 is positioned in a horizontal orientation with leads 14 extending downward from casing 18, the three lowest coordinate leads 14b, 14k, and 14o define virtual sitting plane 60 and have lead standoff values or offset heights of zero. Lead standoff values or offset heights 64a, 64c–64j, 64l–64n, and 64p (collectively or generically, 64) as defined from virtual sitting plane 60 will, therefore, have positive values.

A mathematical transformation that relates the virtual reference coordinate system to the second coordinate system is then determined, and the virtual reference coordinates for each lead 14 of SMT package 10 are subsequently transformed from the virtual reference coordinate system to second system coordinates (sitting or real system coordinates) in the second coordinate system. Skilled persons will recognize that in the second coordinate system of the preferred embodiment, each Z coordinate directly corresponds to the lead standoff value 64 that is used to determine the acceptability of a given SMT package 10.

The coordinate transformation is a basic mathematical technique that is well known to someone skilled in the art and is typically performed with encoded instructions in a digital computing device. In general, a coordinate transformation transforms a set of coordinates from a first coordinate system to a second coordinate system. For instance, the first coordinate system may be Cartesian and the second coordinate system may be polar. In a preferred case, the virtual coordinate system is Cartesian and the second coordinate system is also Cartesian, but translated and rotated with respect to the first. Skilled persons will appreciate that a scaling transformation between the two Cartesian coordinate systems could also be applied, if desired. Skilled persons will also appreciate that calculations could be simplified if the arbitrary reference plane is, or is selected to be, substantially coplanar with major surface 38 of SMT package 10.

In a Cartesian coordinate system, an offset for each point can be described by three numbers: an offset in the X-axis direction, an offset in the Y-axis direction, and an offset in the Z-axis direction. Also, in a Cartesian coordinate system, the general rotation can be considered in terms of the rotation about each axis, such as a rotation of α about the X axis as designated by $R_x(\alpha)$, a rotation of β about the Y axis as designated by $R_y(\beta)$, and a rotation of γ about the Z axis as designated by $R_z(\gamma)$ where the rotation matrices are:

$$R_x(\alpha) = \begin{matrix} 1 & 0 & 0 \\ 0 & \cos(\alpha) & \sin(\alpha) \\ 0 & -\sin(\alpha) & \cos(\alpha) \end{matrix}$$

$$R_y(\beta) = \begin{matrix} \cos(\beta) & 0 & -\sin(\beta) \\ 0 & 1 & 0 \\ \sin(\beta) & 0 & \cos(\beta) \end{matrix}$$

$$R_z(\alpha) = \begin{matrix} \cos(\alpha) & \sin(\alpha) & 0 \\ -\sin(\alpha) & \cos(\alpha) & 0 \\ 0 & 0 & 1 \end{matrix}$$

The lead standoff values 64 can be compared against the maximum acceptable standoff values for any given SMT package 10 and even for any given lead 14 in such an SMT package 10. Skilled persons will appreciate that this and other determination criteria can be derived from the second system coordinates and compared against appropriately constructed look up tables.

An advantage of the present invention is that it can analyze SMT packages 10 as free bodies in space and be used to determine the Z-axis physical reference plane 22 and the real coordinates for leads 14 in any orientation and without reference to pedestal 20 and can do so while SMT package 10 is in continuous motion.

Figure 5:
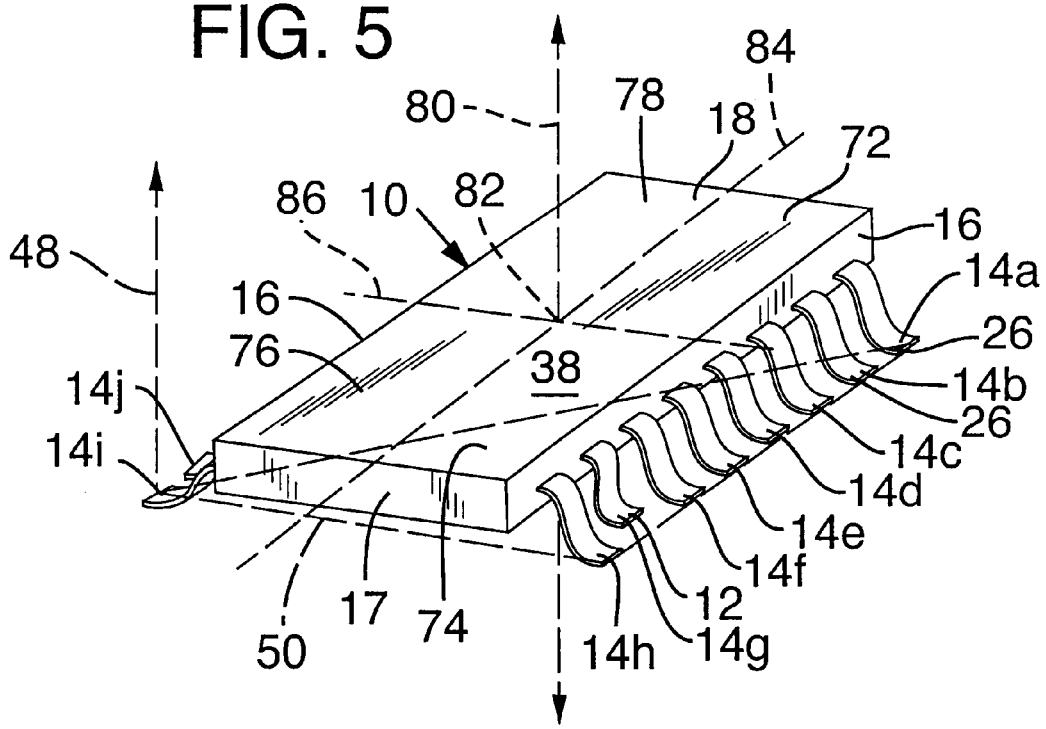
FIG. 5 is a simplified isometric view of the SMT package of FIG. 3 and with referential quadrants and a central axis of rotation.

FIG. 5 is a simplified isometric view of an SMT package 10 showing referential quadrant projections 72, 74, 76, and 78 through casing 18 and a central axis of rotation 80. With reference to FIG. 5, in a preferred embodiment, the sitting plane set having the fourth, fifth, and sixth leads 14 that are used to define the virtual sitting plane 60 of FIG. 4 is also preferably selected to meet the condition of circumscribing the center of mass of casing 18 as projected along the Z axis. Thus the fourth, fifth, and sixth leads 14 preferably have the three lowest coordinate distal portions 26 that circumscribe central axis 80. Accordingly, the virtual sitting plane 90 (FIG. 6) is selected to be coplanar with a triangle formed by joining each of the three lowest coordinate leads 14 that also include the center of mass of SMT package 10 within their triangle.

For the purposes of determining the position of central axis 80 (or, equivalently, centroid 82 or the projection of the center of mass or inertia along the Z axis), skilled persons will find it convenient to assume that SMT package 10 or casing 18 is isotropic in density.

Centroid 82 of SMT package 10, and hence the position of central axis 80, can be computed as the average of respective X- and Y-coordinate limits of the respective major and minor sides 16 and 17: $X_{centroid} = (X_{max} + X_{min})/2$ and $Y_{centroid} = (Y_{max} + Y_{min})/2$. Alternatively, centroid 82 may be determined by summing the individual coordinate positions of leads 14 and dividing the sum by the number leads 14:

$X_{centroid} = \Sigma i=1-N^{Xi}/N$ and $Y_{centroid} = \Sigma i=1-N^{Yi}/N$.

Skilled persons will appreciate that these and other methods to determine centroid 82 are well known in the art and can be employed even when SMT package 10 has a nonrectangular profile.

Skilled persons will also appreciate that numerous selection criteria sequences can be employed to determine the leads 14 that meet the criteria for the circumscribing lowest leads 14, and some of these determinations can be made before, substantially simultaneously with, or after the determination of the position of central axis 80. In one embodiment, all the lead portions 26 are ranked from the lowest to the highest Z coordinate. The two lowest coordinate leads 14 are selected. Then the final lead is selected by moving up the coordinate ranking until a lead 14 is selected that satisfies the center of mass criteria. Skilled persons will further appreciate that these determinations can be made from the first coordinates in the first coordinate system or can be made from the second coordinates in the second coordinate system to determine a new virtual sitting plane.

Figure 6:
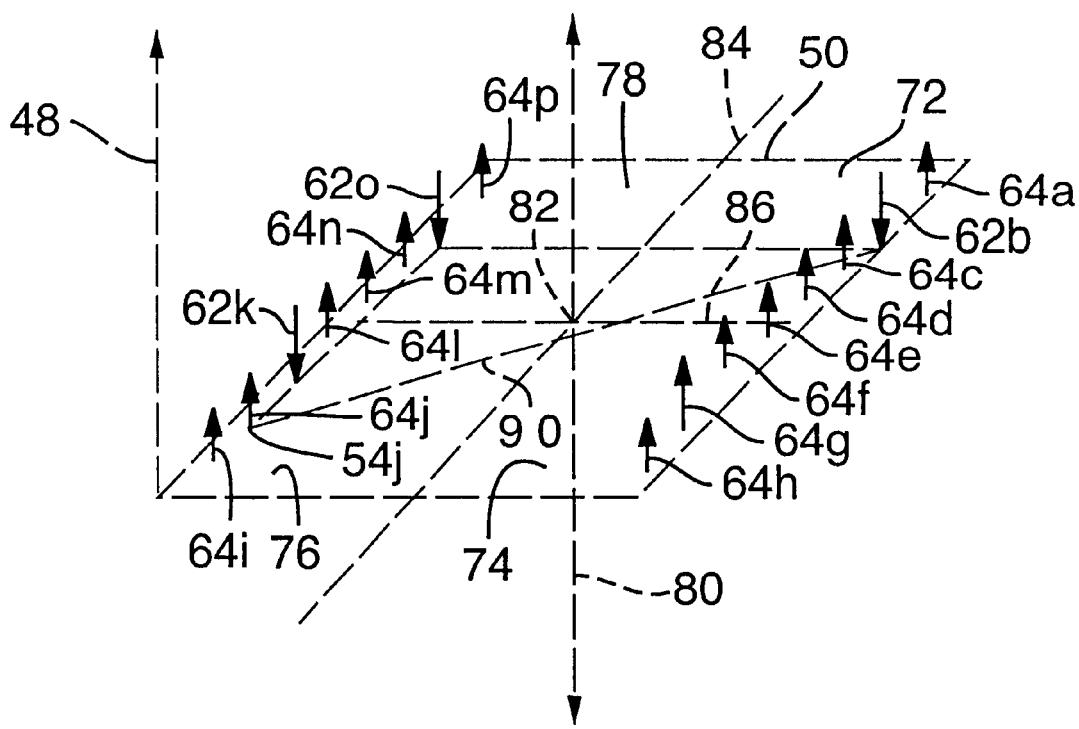
FIG. 6 is a simplified representation of an exemplary second reference plane that circumscribes a central axis.

FIG. 6 is a simplified representation of an exemplary triangle defining virtual sitting plane 90 that circumscribes central axis 80. With reference to FIGS. 5 and 6, in a more preferred embodiment, leads 14 can be grouped into four (or more) quadrant projections 72, 74, 76, and 78 as defined by transverse bisecting axes 84 and 86 along certain axes of symmetry. When SMT package 10 has a rectangular profile, the intersection between axes 84 and 86 can also be used to determine the position of centroid 82. Furthermore, when SMT package 10 has a rectangular profile of the type shown in FIG. 5, then it is a desirable but not necessarily a sufficient condition that only one lead 14 per quadrant projection 72, 74, 76, or 78 can be considered as a candidate for a lead 14 in the virtual sitting plane. In this embodiment, the lowest coordinate lead 14 in each of the respective quadrant projections 72, 74, 76, and 78 is selected. When SMT package 10 has a rectangular profile, there will be four candidate leads 14. These four candidate leads 14 are then ranked from the lowest to the highest coordinate values, and the three lowest coordinate leads 14 are selected to determine the virtual sitting plane. In the case where there is an odd number of leads 14 on each side of SMT package 10, and either of axes 84 or 86 traverse a lead 14, then that lead 14 can be considered to be a member of each of the two adjoining quadrant projections.

With reference briefly to FIG. 4, if the triangle determining virtual sitting plane 60 does not circumscribe central axis 80, a different second reference plane would be selected to meet the criteria of this embodiment. With reference to FIGS. 5 and 6, lead 14$j$ has, for example, the fourth lowest coordinate 54$j$ and the fourth lowest standoff value 64$j$. Thus lead 14$j$ in combination with two other lowest leads 14$b$ and 14$o$ form a triangle that circumscribes central axis 80 and could be used to determine a virtual sitting plane 90 that satisfies this embodiment. Skilled persons will appreciate that in this example with respect to virtual sitting plane,90, the standoff value for lead 14$j$ is zero, lead 14 is negative, and leads 14$a$, 14$c$–14$i$, 14$l$–14$n$, and 14$p$ may be different than with respect to virtual sitting plane 60.

In a case where two or more distinct sets of three leads 14 exist that meet the lowest lead and circumscribing conditions, it may be desirable to calculate the results for multiple cases because these circumstances may describe a bi-stable part. Occasionally an SMT package 10 is produced that does not have one uniquely stable position and rocks between two or more stable positions on a physical plane (like a table in an old diner).

In a preferred embodiment of this invention, SMT packages 10 that may exhibit this behavior are identified so that both or all stable positions may be evaluated for lead standoff values because the lead standoff values may be greater in one stable position than in that of the other. Thus such bi-stable SMT packages 10 are preferably evaluated for both orientations, and then the orientation that produces the greatest departure from the nominal dimensions is evaluated to determine if the SMT package 10 is acceptable.

There are a number of acceptable methods to identify bi-stable SMT packages 10. The simplest method is to assume that every SMT package 10 is bi-stable. In this embodiment, the lowest coordinate lead 14 in each quadrant is determined with respect to an arbitrary reference plane as previously described.

From this quadrant set of four leads 14, all virtual sitting plane sets of leads 14 that also circumscribe the central axis 80 are chosen, and the standoff values 64 for each lead 14 are calculated for each of these virtual sitting planes. The greatest standoff value 64 for each lead 14 is then determined, and the acceptability of the SMT package 10 is determined based on the greatest standoff value 64 for each lead 14.

Figure 7:
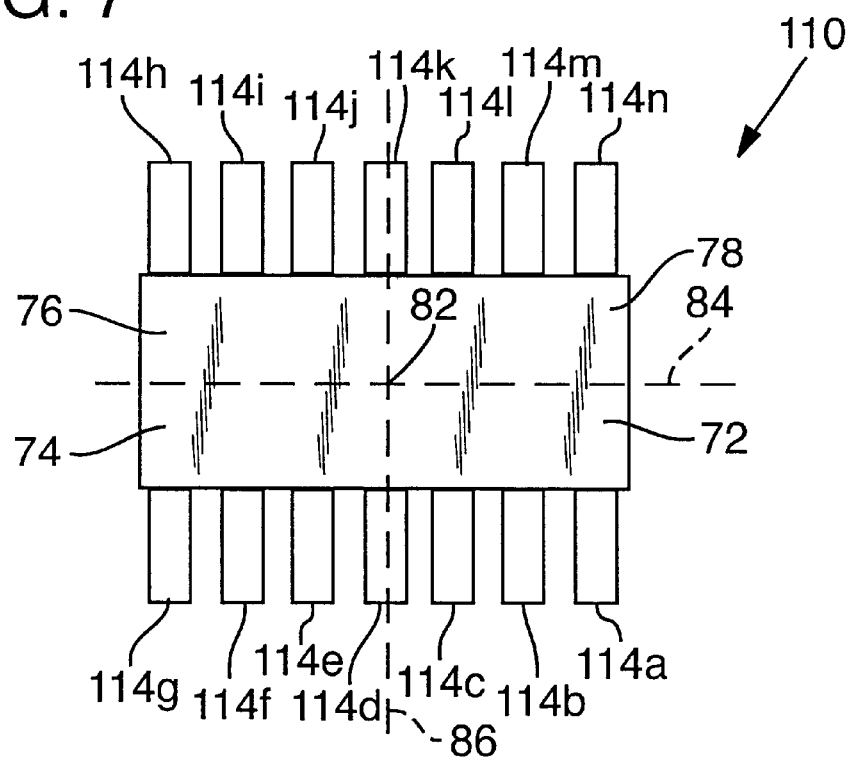
FIG. 7 is a simplified plan view of an SMT package showing quadrant projections useful for determining whether an SMT package is bi-stable.

FIG. 7 is a simplified plan view of SMT package 110 useful for presenting an example of determining whether SMT package 110 is bi-stable. In the example, the designation of leads 114 has been abbreviated by only the letter designation to simplify the example.

BI-STABLE INQUIRY

EXAMPLE 1

For convenience, it is given that the following leads 114 are determined to be the lowest by quadrant projection: Quadrant 72-lead b, Quadrant 74-lead g, Quadrant 76-lead i, and Quadrant 78-lead m. Therefore, the potential trios are <b,g,i>, <g,i,m>, <b,g,m>, and <b,i,m>. The trio <g,i,m> is eliminated because it does not enclose centroid 82.

The remaining trios are all considered candidate sitting plane sets or "tripods" that can support SMT package 110 on a planar surface. Each tripod is in turn used to mathematically construct a virtual sitting plane from which the lead standoff values 64 of all the remaining leads 114 are calculated. While this technique works fine, it lacks elegance and consumes greater computational resources than an alternative preferred embodiment described below.

A simple refinement of this method is to determine which two leads 114 are in contact with the virtual sitting plane in each stable position. In this embodiment, the lowest coordinate lead 114 in each quadrant is determined as described above.

Figure 8:
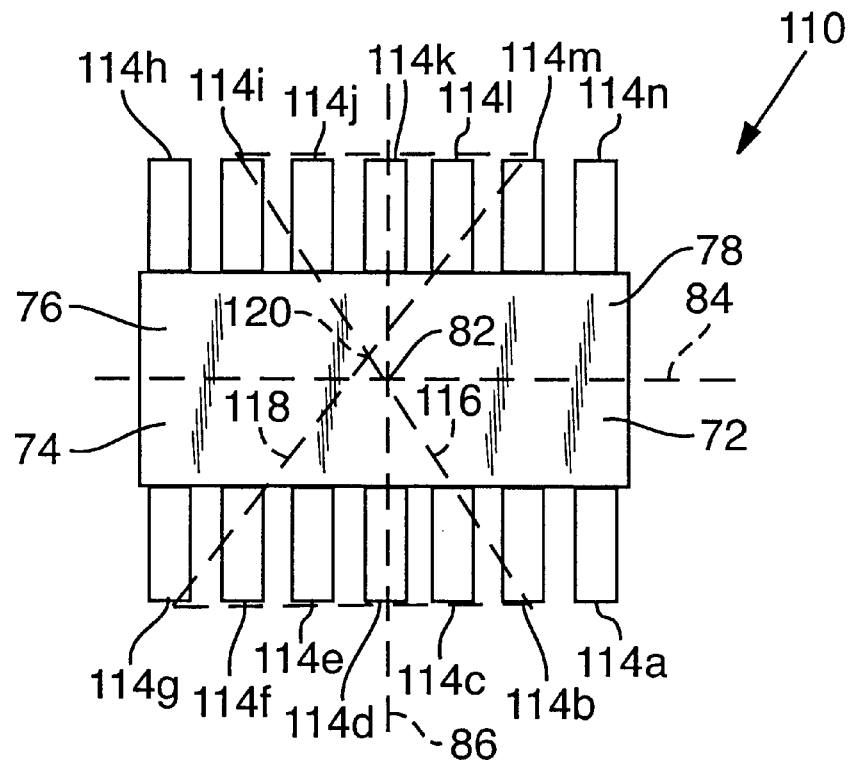
FIG. 8 is a simplified plan view of an SMT package showing a rocking axis useful for determining whether an SMT package is bi-stable and has acceptable lead standoff values.

FIG. 8 is a simplified plan view of SMT package 110 useful for presenting an alternative example of determining whether SMT package 110 is bi-stable. With reference to FIG. 8, lines 116 and 118 that connect the pairs of diagonally opposed quadrant lowest leads 114 are mathematically constructed, and the intersection 120 of lines 116 and 118 in X and Y is mathematically determined. Then the pair of leads 114 of the line 116 or 118 that has the lowest Z value at intersection 120 is determined and selected to be the rocking axis. The lead standoff values 64 for each lead 114 are then calculated using the virtual sitting plane for each of the two candidate trios of leads 114 that include the selected rocking axis. The greatest stand-off value 64 for each lead 114 is determined, and the acceptability of the SMT package 110 is determined based on the greatest standoff values 64.

In the example below, the designation of leads 114 has been abbreviated by only the letter designation to simplify the example.

BI-STABLE INQUIRY

EXAMPLE 2

For convenience, it is given that the following leads 114 are determined to be the lowest by quadrant projection: Quadrant 72-lead b, Quadrant 74-lead g, Quadrant 76-lead i, and Quadrant 78-lead m. The following lead pairs are selected from the lowest leads of diagonally opposed quadrants: Quadrants 72 and 76-<b,i> (line 116) and Quadrants 74 and 78-<g,m> (line 118).

Within a three-dimensional mathematical construct, it is determined that <g,m> line 116 is lower than <b,i > line 118 at X-Y intersection 120. Hence the potential trios are <g,i,m> and <b,g,m> as they contain the pair <g,m>. The trio <g,i,m> is eliminated, as it does not enclose the centroid 82. The trio of <b,g,m> is selected to be the only valid tripod that can support SMT package 110 on a planar surface. It is used to mathematically construct a virtual sitting plane from which the lead standoff values 64 of all the remaining leads 114 are calculated.

Skilled persons will appreciate that if <b,i> line 118 had been determined to be lower than <g,m> line 116, then both <b,g,i> and <b,i,m> would be considered valid trios, and SMT package 110 would be considered to be bi-stable. Both <b,g,i> and <b,i,m> would be used, in turn, to calculate a sitting plane, and standoff values 64 calculated for the other leads 114 for both cases.

Skilled persons will also appreciate that the determinations for lowest leads 14 or their Z coordinates are preferably made from the first coordinates in the first coordinate system; however, the second coordinates in the second coordinate system could also be used to determine new virtual sitting planes.

As mentioned above, the lead standoff values 64 can be compared against the maximum acceptable standoff values for any given SMT package 10 and even for any given lead 14 in such an SMT package 10. Skilled persons will appreciate that this and other determination criteria can be derived from the second system coordinates and compared against appropriately constructed look up tables.

It will be obvious to those having skill in the art that many changes may be made to the details of the above-described embodiment of this invention without departing from the underlying principles thereof. The scope of the present invention should, therefore, be determined only by the following claims.

What is claimed is:

1. A method for determining the acceptability of the positions of leads of an IC device, each of the leads having a distal portion, comprising:

defining a virtual reference plane in a first coordinate system;

determining, in the first coordinate system, first system coordinates of the distal portions of leads with respect to the virtual reference plane;

analyzing the first system coordinates to select a sitting plane set of distal portions of three of the leads to define a virtual sitting plane in a second coordinate system;

transforming the first system coordinates of the distal portion of each lead to second system coordinates in the second coordinate system; and analyzing the second system coordinates of the distal portions of the leads to determine the acceptability of the IC device.

2. The method of claim 1 in which the virtual reference plane is transverse to a Z dimension and the sitting plane set of distal portions is selected from the distal portions having the lowest coordinate values in the Z dimension.

3. The method of claim 1 in which the IC device comprises a Z dimension that is transverse to the virtual reference plane, a center of mass, and a virtual Z axis that passes through the center of mass and projects along the Z dimension, the method further comprising:

selecting the sitting plane set of distal portions from a set of three distal portions having low coordinate values in the Z dimension and circumscribing the virtual Z axis.

4. The method of claim 3 further comprising:

dividing the IC device into at least three virtual sections containing one or more leads based on the first system coordinates; and selecting the sitting plane set of distal portions such that each distal portion in the sitting plane set belongs to a different virtual section.

5. The method of claim 4 further comprising:

determining virtual rocking lines between pairs of distal portions having the lowest coordinate values in the Z dimension in diagonally opposed virtual sections;

determining an intersection of the virtual rocking lines;

determining and selecting the virtual line that has the lowest coordinate value in the Z dimension at the intersection;

determining one or more virtual sitting planes with respective second coordinate systems from the distal portions on the selected virtual rocking line;

transforming the first system coordinates of the distal portions of each lead to second system coordinates in each of the second coordinate systems;

analyzing the second system coordinates of the distal portions with respect to the respective virtual sitting plane to determine a greatest standoff value for each distal portion; and determining the acceptability of the IC device based on the greatest standoff values for each distal portion.

6. The method of claim 1 further comprising:

selecting a reference set of distal portions of three spaced-apart leads to define the virtual reference plane in the first coordinate system.

7. The method of claim 6 further comprising:

selecting the reference set of distal portions from three leads having the greatest distances between them.

8. The method of claim 6 in which the sitting plane set of distal portions contains at least one distal portion that is not in the reference set of distal portions.

9. The method of claim 1 in which the relative coplanarity of the distal portion of each lead is determined while the IC device is in motion.

10. The method of claim 9 further comprising:

employing a light source to provide illumination of the IC device for less than one second.

11. The method of claim 9 in which an image sensor acquires position data of the distal portions of the leads in a short period of time.

12. The method of claim 1 in which the IC device is substantially enclosed within a generally rectangular parallelepipedal hexahedral package having a major surface that separates two side surfaces and in which the leads comprise J or gull wing leads that protrude from the side surfaces.

13. The method of claim 1 further comprising:

employing an image sensor to obtain a two-dimensional view of the leads.

14. The method of claim 13 further comprising:

employing one or more mirrors or prisms to combine two or more views of the IC device onto the image sensor.

15. The method of claim 1 in which the relative coplanarity of the distal portion of each lead is determined while neither the virtual reference plane nor the virtual sitting plane is horizontal.

16. The method of claim 1 further comprising:

determining from the system coordinates whether the IC device comprises more than one virtual sitting plane.

17. The method of claim 16 further comprising:

analyzing the distal portions with respect to each virtual sitting plane to determine the acceptability of the device.

18. A system for determining coplanarity of leads of an IC device substantially enclosed within a surface mount package (SMT package) having a major surface between two side surfaces that generally defines a package plane; the leads protruding from the two side surfaces and having distal portions at positions at respective distances from the package plane; the leads including a sitting plane set of leads whose distal portions define a sitting plane, comprising:

a package carrier for transporting the SMT package through a predetermined location;

a light source for illuminating the leads of the SMT package when the SMT package is in the predetermined location;

one or more image sensors capable of obtaining position data of positions of the distal portions of the leads with respect to each other; and a computing device that receives the position data; that determines, in a first coordinate system, a virtual reference plane; that determines, in the first coordinate system, first system coordinates of the distal portions of all the leads with respect to the virtual reference plane; that analyzes the first system coordinates to identify the distal portions of the sitting plane set of leads to identify the sitting plane and define it in a second coordinate system; that transforms the first system coordinates of the distal portion of each lead to second system coordinates in the second coordinate system; and that compares the second system coordinates of each distal portion to the sitting plane to determine the relative coplanarity of the distal portion of each lead.

19. The system of claim 18 in which a reference set of distal portions of three spaced-apart leads is selected to define the virtual reference plane in the first coordinate system.

20. The system of claim 19 in which the reference set of distal portions is selected from a set of three leads having the greatest distances between them.

21. The system of claim 19 in which one or more mirrors or prisms are employed to combine two or more views of the SMT package onto the two-dimensional image sensor.

22. The system of claim 19 in which the SMT package comprises a generally rectangular parallelepipedal hexahedral shape.

23. The system of claim 22 in which the SMT package comprises two minor side surfaces and the leads are deployed about the four side surfaces of the SMT package.

24. The system of claim 19 in which the sitting plane set of leads comprises at least one lead that is not in the reference set of leads.

25. The system of claim 18 in which the package plane is selected to define the virtual reference plane in the first coordinate system.

26. The system of claim 18 in which the image sensor has a focal plane that is selected to define the virtual reference plane in the first coordinate system.

27. The system of claim 18 in which the image sensor comprises a video camera or a focal-plane array sensor.

28. The system of claim 18 in which the leads comprise J or gull wing leads.

29. The system of claim 18 in which the computing device comprises a digital computing device.

30. The system of claim 18 in which the SMT package is in motion relative to the image sensor and the light source illuminates the SMT package for a short duration of time.

31. The system of claim 18 in which the image sensor acquires the position data of the distal portions of the leads in a short period of time.

32. The system of claim 18 in which the relative coplanarity of the distal portion of each lead is determined while neither the virtual reference plane nor the sitting plane is horizontal.

33. The system of claim 18 in which the IC device comprises a Z dimension that is transverse to the virtual reference plane, a center of mass, and a virtual Z axis that passes through the center of mass and projects along the Z dimension; and in which the sitting plane set of distal portions is selected from a set of three distal portions having low coordinate values in the Z dimension and circumscribing the virtual Z axis.

34. The system of claim 18 in which the IC device comprises more than one sitting plane.

35. The system of claim 34 in which the distal portions with respect to each sitting plane are analyzed to determine the acceptability of the IC device.

36. The system of claim 18 in which the IC device is virtually divided into at least three virtual sections containing one or more leads based on the first system coordinates, and the sitting plane set of distal portions is selected such that each distal portion in the sitting plane set belongs to a different virtual section.

37. The system of claim 36 further comprising:

determining virtual rocking lines between pairs of distal portions having the lowest coordinate values in the Z dimension in diagonally opposed virtual sections;

determining an intersection of the virtual rocking lines;

determining and selecting the virtual line that has the lowest coordinate value in the Z dimension at the intersection;

determining one or more virtual sitting planes with respective second coordinate systems from the distal portions on the selected virtual rocking line;

transforming the first system coordinates of the distal portions of each lead to second system coordinates in each of the second coordinate systems;

analyzing the second system coordinates of the distal portions with respect to the respective virtual sitting plane to determine a greatest standoff value for each distal portion; and determining the acceptability of the IC device based on the greatest standoff values for each distal portion.

* * * * *